US008852858B2

(12) United States Patent
Sogard

(10) Patent No.: US 8,852,858 B2
(45) Date of Patent: Oct. 7, 2014

(54) METHODS AND DEVICES FOR HYBRIDIZATION AND BINDING ASSAYS USING THERMOPHORESIS

(75) Inventor: Michael Sogard, Menlo Park, CA (US)

(73) Assignee: Nikon Research Corporation of America, Belmont, CA (US)

( * ) Notice: Subject to any disclaimer, the term of this patent is extended or adjusted under 35 U.S.C. 154(b) by 82 days.

(21) Appl. No.: 11/811,279

(22) Filed: Jun. 7, 2007

(65) Prior Publication Data

US 2008/0009071 A1   Jan. 10, 2008

Related U.S. Application Data

(62) Division of application No. 10/038,342, filed on Oct. 23, 2001, now Pat. No. 7,244,611.

(51) Int. Cl.
*C12Q 1/68* (2006.01)
*G01N 21/17* (2006.01)
*G01N 21/64* (2006.01)
*B01L 7/00* (2006.01)

(52) U.S. Cl.
CPC .......... *B01L 7/54* (2013.01); *B01L 2300/0877* (2013.01); *B01L 2300/1805* (2013.01); *B01L 2300/1838* (2013.01); *B01L 2300/0636* (2013.01); *C12Q 1/6837* (2013.01)
USPC ............... 435/4; 435/6; 435/6.11; 435/287.2; 435/286.7

(58) Field of Classification Search
CPC .................. C12Q 2537/143; C12Q 2565/629; C12Q 1/6832; C12Q 1/6837; B01L 7/52; B01L 7/54; B01L 2400/0451; B01L 2400/0442; B01L 2300/0636; B01L 2300/0877; B01L 2300/1805; B01L 2300/1838

USPC ............ 435/6, 6.11, 287.2, 286.7, 4; 137/344
See application file for complete search history.

(56) References Cited

U.S. PATENT DOCUMENTS

| 5,158,690 A | 10/1992 | Batchelder et al. |
| 5,559,221 A | 9/1996 | Agrawal et al. |
| 5,585,277 A | 12/1996 | Bowie et al. |
| 5,736,025 A | 4/1998 | Smith et al. |

(Continued)

FOREIGN PATENT DOCUMENTS

| DE | 36 22 591 C2 | 1/1998 |
| WO | WO 89/10977 | 11/1989 |
| WO | WO 00/61261 | 10/2000 |

OTHER PUBLICATIONS

Duhr et al., Eur. Phys. J. E 15:277-286 (2004).*

(Continued)

*Primary Examiner* — Sharmila G. Landau
*Assistant Examiner* — Shannon Janssen
(74) *Attorney, Agent, or Firm* — Law Office of Salvatore Arrigo and Scott Lee, LLP

(57) ABSTRACT

Methods for performing a hybridization assay between a target biomolecule and an array comprising a surface to which are attached biomolecular probes with different, known sequences, at discrete, known locations, the method comprising: providing a container holding a hybridization mixture comprising the target biomolecule and also holding the array; and creating a temperature gradient in the hybridization mixture oriented within the container such that at least a portion of the target biomolecule is driven onto the surface of the array.

26 Claims, 3 Drawing Sheets

(56) References Cited

U.S. PATENT DOCUMENTS

| | | | |
|---|---|---|---|
| 5,795,720 | A | 8/1998 | Henco et al. |
| 5,849,486 | A | 12/1998 | Heller et al. |
| 6,020,141 | A | 2/2000 | Pantoliano et al. |
| 6,045,996 | A * | 4/2000 | Cronin et al. ............... 506/4 |
| 6,114,122 | A | 9/2000 | Besemer et al. |
| 6,214,187 | B1 | 4/2001 | Hammond et al. |
| 6,280,967 | B1 | 8/2001 | Ransom et al. |
| 6,589,740 | B2 | 7/2003 | Nakao et al. |
| 6,642,000 | B1 * | 11/2003 | Strizhkov et al. ............ 435/6.12 |
| 6,733,729 | B2 | 5/2004 | Blumenfeld et al. |
| 6,749,814 | B1 | 6/2004 | Bergh et al. |
| 7,081,192 | B1 * | 7/2006 | Wang et al. ................ 204/547 |
| 7,172,897 | B2 * | 2/2007 | Blackburn et al. ......... 435/287.2 |
| 7,244,611 | B2 | 7/2007 | Sogard |
| 2001/0036672 | A1 | 11/2001 | Anderson et al. |
| 2003/0077599 | A1 | 4/2003 | Sogard |

OTHER PUBLICATIONS

Zheng et al., Journal of Nanobiotechnology, 3:1-10 (2005).*
McNab et al. "Thermophoresis in Liquids," Journal of Colloid and Interface Science, 44(2): 339-346 (1973).
Ke et al., "The Thermal Stability of DNA Fragments with Tandem Mismatches as a d(CXYG)-d(CY'X'G) Site," Nucleic Acids Research, 24(4): 707-712 (1996).
Zhu et al., "The Relative Stabilities of Base Pair Stacking Interactions and Single Mismatches in Long RNA Measured by Temperature Gradient Gel Electrophoresis," Biochemistry, 36: 15326-15335 (1997).
Bierlein, "A Phenomenological Theory of the Soret Diffusion," Journal of Chemical Physics, 33(1): 10-14 (1955).
Giddings et al., "Measurement of Thermal Diffusion Factors by Thermal Field-Flow Fractionation," Journal of Physical Chemistry, 74(24): 4291-4294 (1970).
Giglio et al., "Soret-Type Motion of Macromolecules in Solution," Physical Review Letters 38(1): 26-30 (1977).
Gurrieri et al., "Real-time imaging of the reorientation mechanisms of YOYO-labelled DNA molecules during 90° and 120° pulsed field gel electrophoresis," Nucleic Acids Research, 24(23): 4759-4767 (1996).
Köhler et al., "Aspects of Thermal Diffusion Forced Rayleigh Scattering: Heterodyne Detection, Active Phase Tracking, and Experimental Constraints," J. Phys. Chem., 99: 5838-5847 (1995).
Pluen et al., "Diffusion of Macromolecules in Agarose Gels: Comparison of Linear and Globular Configurations," Biophysical Journal, 77: 542-552 (1999).
Schimpf et al., "Characterization of Thermal Diffusion in Polymer Solutions by Thermal Field-flow Fractionation: Dependence on Polymer Solvent Parameters," J. Polymer Science, Part B, Polymer Physics, 27: 1317-1332 (1989).
Schimpf et al., "Characterization of Thermal Diffusion of Copolymers in Solution by Thermal Field-Flow Fractionation," J. Polymer Science: Part B: Polymer Physics, 28: 2673-2680 (1990).
Schimpf et al., "Mechanism of Polymer Thermophoresis in Nonaqueous Solvents," J. Phys. Chem. B, 104 9935-9942 (2000).
Murphy, "Gene expression Studies Using Microarrays: Principles, Problems, and Prospects," Adv. Physiol. Educ., 26(4): 256-270 (2002).
Bielenberg et al., "A hydrodynamic/Brownian motion model of thermal diffusion in liquids," Physica A 356: 279-293 (2005).
Braun et al., "Trapping of DNA by Thermophoretic Depletion and Convection," Phys. Rev. Lett. 89(18): 188103-1-188103-4 (2002).
Liu et al., "Acoustic micromixer for enhancement of DNA biochip systems," J. Microlith., Microfab., Microsyst., 2(3): 178-184 (2003).
Day, "Thermal Gradients Can Boost the Local Concentration of DNA in Solution," Physics Today 16-17 (2003).
Liu, "Gene Array Technologies in Biological Investigations," Proceedings of the IEEE, 93(4): 737-749 (2005).
Ananthaswamy, "Swirling hot water in the ocean floor may have given evolution a kick-start," New Scientist, 176(2367): 15 (2002).
Preliminary Amendment filed Feb. 9, 2006, in U.S. Appl. No. 11/339,941.
Specification filed Jan. 25, 2006, in U.S. Appl. No. 11/339,941.
Notice of Allowance and Fee(s) Due and Notice of Allowability, mailed Mar. 15, 2007, in U.S. Appl. No. 10/038,342 (now U.S. Patent 7,244,611).
Supplemental Response filed Jan. 5, 2007, in U.S. Appl. No. 10/038,342 (now U.S. Patent 7,244,611).
Interview Summary mailed Dec. 19, 2006, in U.S. Appl. No. 10/038,342 (now U.S. Patent 7,244,611).
Request for Continued Examination filed Nov. 3, 2006, in U.S. Appl. No. 10/038,342 (now U.S. Patent 7,244,611).
Reply to Final Office Action filed Oct. 18, 2006, in U.S. Appl. No. 10/038,342 (now U.S. Patent 7,244,611).
Final Office Action mailed May 4, 2006, in U.S. Appl. No. 10/038,342 (now U.S. Patent 7,244,611).
Response to Restriction Requirement filed Feb. 6, 2006, in U.S. Appl. No. 10/038,342 (now U.S. Patent 7,244,611).
Office Action mailed Jan. 4, 2006, in U.S. Appl. No. 10/038,342 (now U.S. Patent 7,244,611).
Response filed Sep. 1, 2005, in U.S. Appl. No. 10/038,342 (now U.S. Patent 7,244,611).
Notice of Non-responsive Amendment mailed Aug. 3, 2005, in U.S. Appl. No. 10/038,342 (now U.S. Patent 7,244,611).
Response filed May 17, 2005, in U.S. Appl. No. 10/038,342 (now U.S. Patent 7,244,611).
Office Action mailed Feb. 18, 2005, in U.S. Appl. No. 10/038,342 (now U.S. Patent 7,244,611).
Response to Election/Restriction Requirement filed Nov. 17, 2003, in U.S. Appl. No. 10/038,342 (now U.S. Patent 7,244,611).
Interview Summary mailed Oct. 30, 2003, in U.S. Appl. No. 10/038,342 (now U.S. Patent 7,244,611).
Office Action mailed Sep. 30, 2003, in U.S. Appl. No. 10/038,342 (now U.S. Patent 7,244,611).
Preliminary Amendment filed Mar. 14, 2003, in U.S. Appl. No. 10/038,342 (now U.S. Patent 7,244,611).
Duhr et al., Eur. Phys. J. E, vol. 15, pp. 277-86 (2004).
Zheng et al., Journal of Nanobiotechnology, vol. 3, pp. 1-10 (2005).
Office Action mailed May 18, 2011, in U.S. Appl. No. 11/339,941, filed Jan. 25, 2006.
Office Action mailed Jan. 20, 2011, in U.S. Appl. No. 11/339,941, filed Jan. 25, 2006.
Notice of Panel Decision from Pre-Appeal Brief Review, mailed Oct. 15, 2010, in U.S. Appl. No. 11/339,941, filed Jan. 25, 2006.
Office Action mailed Jun. 9, 2010, in U.S. Appl. No. 11/339,941, filed Jan. 25, 2006.
Office Action mailed Aug. 7, 2009, in U.S. Appl. No. 11/339,941, filed Jan. 25, 2006.
Office Action mailed Dec. 24, 2008, in U.S. Appl. No. 11/339,941, filed Jan. 25, 2006.
Terminal Disclaimer filed May 9, 2008, in U.S. Appl. No. 11/339,941, filed Jan. 25, 2006.
Office Action mailed Feb. 11, 2008, in U.S. Appl. No. 11/339,941, filed Jan. 25, 2006.
Office Action mailed Oct. 16, 2007.

* cited by examiner

METHODS AND DEVICES FOR HYBRIDIZATION AND BINDING ASSAYS USING THERMOPHORESIS

This application is a divisional of U.S. patent application Ser. No. 10/038,342, filed Oct. 23, 2001 now U.S. Pat. No. 7,244,611, which is incorporated herein by reference in its entirety.

BACKGROUND OF THE INVENTION

This invention relates to methods for improving the discrimination of hybridization of target molecules to probes on substrate-bound oligonucleotide, peptide, or protein arrays. Therefore, it relates to the fields of molecular biology and biophysics.

An efficient method of sequencing DNA is by means of hybridization to known nucleotide sequences arranged in microarrays. See e.g., PCT WO 89/10977. In this method a solution of single strands of unknown DNA is mixed with an array of oligonucleotides which are fixed to a substrate. The oligonucleotides vary in sequence, and each unique sequence occupies a small region on the substrate whose position is known. If the sequence of a given oligonucleotide region is complementary to the unknown DNA sample, then the DNA strands will hydrogen bond or hybridize to the oligonucleotides at that site. Since the oligonucleotide sequence is known, that part of the sample which bound to the oligonucleotide is then determined as well. If the DNA sample is fragmented into lengths comparable to the lengths of the oligonucleotides, then the entire DNA sample can, in principle, be sequenced.

The sites in the microarray at which the DNA binds can be identified by attaching tags to the sample fragments before hybridization. These tags can be radioactive, fluorescent, or luminescent, for example. By scanning the hybridized microarray for radioactivity or fluorescence, the hybridized sites can be identified.

The power of this technology lies in the discriminatory ability of the hybridization process. For DNA fragments on the order of 20 nucleotides in length or less, a single mismatch in nucleotide base pairs can significantly affect the hybridization process, and more than one adjacent base pair mismatch can effectively prevent hybridization. The degree of discrimination is controlled by the conditions in the solution: the types and concentrations of buffers and the temperature. The degree to which nucleic acids hybridize is referred to as "stringency". In a state of high stringency conditions, hybridization rate is reduced and the probability of base pair mismatches is reduced even more. In a condition of low stringency, hybridization becomes more likely and the probability of base pair mismatches increases. In general, high stringency conditions and high discrimination against base pair mismatches are characterized by higher temperature, lower ionic strength, low reactant concentration, and short reaction times. In addition, many washings of the microarray with hybridization buffers are done to remove sample DNA strands which have not hybridized to probe oligonucleotides.

The initial DNA sample is often very limited in size, and to increase the probability of detecting a successful hybridization in the microarray, the DNA is amplified using polymerase chain reaction (PCR) or other means. Despite the amplification process, the DNA concentration is often still very limited, so hybridization of a substantial fraction of the sample may be needed for reliable detection. Thus conditions of high stringency may also limit the detectability of hybridized samples.

Hybridization rates in the microarray are ultimately limited by diffusion of the DNA samples in their buffer to the substrate. More specifically, the microarray is mounted within a structure (i.e., a cell) which serves as a reservoir for the DNA sample. Various techniques are used to circulate the samples within the cell to expedite hybridization, such as circulation of the sample from the cell to an external reservoir and back, or by agitation of the cell, but hybridization times can still be many hours. Furthermore, washing the microarray in buffer to remove DNA samples which did not hybridize to oligonucleotide sites, thereby increasing the stringency conditions, can take a comparable amount of time. See, for example, U.S. Pat. No. 6,114,122.

One technique to speed things up is to use eletrophoresis to attract the negatively charged DNA samples to the oligonucleotides. This requires adding electrodes and an electrical grid to the microarray, so that an electric field with the right polarity can be established to attract the DNA to the oligonucleotides. The electrical mobility of the DNA can be much greater than the intrinsic diffusion rate in solution. After hybridization has taken place, the polarity of the field can be reversed, thereby driving the non-hybridized DNA samples away from the microarray, and making the washing steps more effective. This can greatly increase the stringency of the process while reducing the overall hybridization time. See, e.g., U.S. Pat. No. 5,849,486.

However, these improvements are purchased at the expense of added complexity. The microarray must be provided with an electrical grid. Moreover, the grid must be covered by a permeation layer which isolates and protects the DNA from the metallic grid, excludes electrolysis products from the DNA buffer, and provides support for the oligonucleotide probes. High density microarrays are typically scanned for fluorescence through their transparent substrates. This is not possible if an electrical grid is present. The buffer properties must be adjusted to accommodate the electrophoresis. In particular, the buffer electrical conductivity must not be low. These constraints may not permit using buffers which are optimal for hybridization.

The concept of a microarray to identify unknown samples can be extended to other molecules such as proteins. In the technique known as ELISA (enzyme linked immunosorbent assay), an array of known antibodies is created on a substrate. The array is then exposed to a solution of unknown proteins (i.e., antigens). After washing, proteins which remain bound to their corresponding antibodies can be fluorescently tagged, and identified from their locations in the array. While electrophoresis can be used here, the variety of charge states of different proteins complicates the experiments.

Temperature gradient gel electrophoresis, as described in German Application DE-OS 36 22 591, is a method for detecting slight structural differences or peculiarities of biological macro-molecules such as nucleic acids or proteins. This technique relies upon the use of temperature gradients in combination with electrophoresis for the separation of biological macro-molecules. This technique, however, is restricted to the operation of flat-bed gel electrophoresis.

Thermophoresis refers to a process in which particles, residing in a gas supporting a temperature gradient, are driven away from warm surfaces toward cooler surfaces. The thermophoretic drift velocity is found to be directly proportional to the temperature gradient in the gas. Although the phenomenon has been well studied with aerosols, there has been little reported on the use of thermophoresis with particles in liquid. McNab et al. (1973) J. Colloid and Interface Science 44:339 have presented an equation describing thermophoretic drift velocity based on a study of small latex spheres in water and hexane. No dependence on particle size was detected within the limited particle size range studied. The thermophoretic drift velocity was found to be directly proportional to the temperature gradient in the fluid.

Thus, there is still a need for methods for improving the stringency of and/or decreasing the time required for hybridization experiments. The present invention addresses this and other needs.

SUMMARY OF THE INVENTION

The present invention provides a method for performing a hybridization assay between a target nucleic acid molecule and an oligonucleotide array. The array comprises surface to which are covalently attached oligonucleotide probes with different, known sequences, at discrete, known locations. The method comprises the step of contacting or incubating the array with a hybridization mixture comprising the target, and optionally an isostabilizing agent, under thermophoretic conditions and determining the identity of probes to which the target has hybridized. Preferably, the thermophoretic conditions comprise the application of a temperature gradient perpendicular to the array surface whereby the target is driven to the array surface. The method also may further comprise the step of reversing the temperature gradient, whereby any unhybridized target is driven away from the array surface.

Preferably, the target further comprises a detectable label and the array has a density of at least ten thousand features per square cm. In one embodiment, the array surface is vertical and the temperature gradient is horizontal. In another embodiment, the array surface is horizontal and the temperature gradient is vertical. Preferably, a temperature gradient of about 10° C./mm is used.

The invention also provides a method for performing a hybridization assay between a target nucleic acid molecule and an oligonucleotide array, the array comprising a surface to which are covalently attached oligonucleotide probes with different, known sequences, at discrete, known locations, wherein such probes have been contacted with a hybridization mixture comprising the target nucleic acid molecule. The method comprises the steps of: applying a temperature gradient to the array surface whereby any unhybridized target is driven away from the array surface; and determining the identity of probes to which the target has hybridized.

A method for performing a binding assay between a target molecule and an array is also provided. According to this embodiment, the array comprises a surface to which are covalently attached a plurality of binding partners with different, known sequences, at discrete, known locations. The method comprises the steps of: incubating the array with a mixture comprising the target under thermophoretic conditions; and determining the identity of binding partners to which the target has bound.

Apparatus for performing the various methods described above are also provided. The apparatus preferably will comprise a container connected to at least one temperature control blocks in a heat-conducting fashion, such that a temperature gradient is produced. The container may be connected to two temperature control blocks in a heat-conducting fashion and may further comprise an inlet port and an outlet port.

DETAILED DESCRIPTION OF THE INVENTION

General

Figure 1:
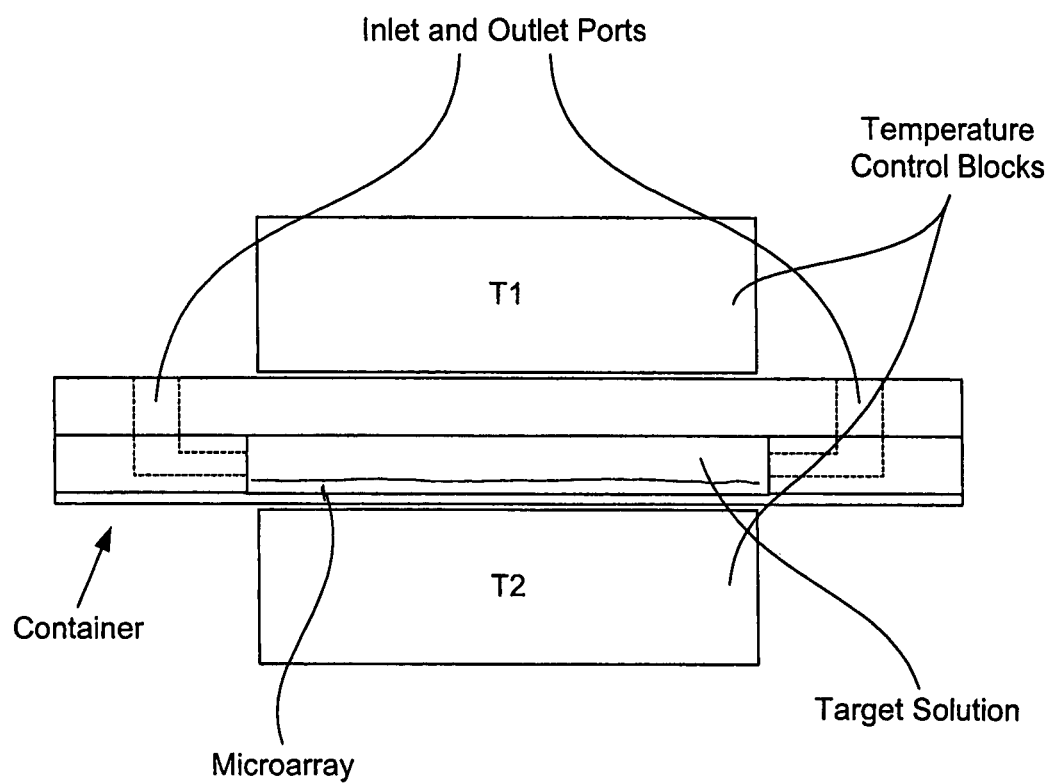
FIG. 1 shows an embodiment of the invention wherein a hybridization cell oriented horizontally is installed between two temperatures reservoirs.

It is to be understood that the terminology used herein is for the purpose of describing particular embodiments only and is not intended to limit the scope of the present invention which will be limited only by the appended claims. It must be noted that as used herein and in the appended claims, the singular forms "a", "an", and "the" include plural reference unless the context clearly dictates otherwise. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described.

Definitions

"Complementary" refers to the topological compatibility or matching together of interacting surfaces of a probe molecule and its target. Thus, the target and its probe can be described as complementary, and furthermore, the contact surface characteristics are complementary to each other.

"Denaturing agent" refers to compositions that lower the melting temperature of double stranded nucleic acid molecules by interfering with hydrogen bonding between bases in a double-stranded nucleic acid or the hydration of nucleic acid molecules. Denaturing agents can be included in hybridization buffers at concentrations of about 1 M to about 6 M and, preferably, about 3 M to about 5.5 M.

"Denatured nucleic acid" refers to a nucleic acid which has been treated to remove folded, coiled, or twisted structure. Denaturation of a triple-stranded nucleic acid complex is complete when the third strand has been removed from the two complementary strands. Denaturation of a double-stranded DNA is complete when the base pairing between the two complementary strands has been interrupted and has resulted in single-stranded DNA molecules that have assumed a random form. Denaturation of single-stranded RNA is complete when intramolecular hydrogen bonds have been interrupted and the RNA has assumed a random, non-hydrogen bonded form.

"Feature" refers to an area of a substrate having a collection of same-sequence, surface-immobilized molecules. One feature is different than another feature if the probes of the different features have different sequences of component molecules.

"Fluorescence probe molecule" refers to a fluorophore, which is a fluorescent molecule or a compound which is capable of binding to an unfolded or denatured receptor and, after excitement by light of a defined wavelength, emits fluorescent energy. The term fluorescence probe molecule encompasses all fluorophores. More specifically, for proteins, the term encompasses fluorophores such as thioinosine, and N-ethenoadenosine, formycin, dansyl derivatives, fluorescein derivatives, 6-propionyl-2-(dimethylamino)-napthalene (PRODAN), 2-anilinonapthalene, and N-arylamino-naphthalene sulfonate derivatives such as 1-anilinonaphthalene-8-sulfonate (1,8-ANS), 2-annilinonaphthalene-6-sulfonate(2, 6-ANS), 2-aminonaphthalene-6-sulfonate, N,N-methyl-2- aminonaphthalene-6-sulfonate, N-phenyl-2-aminonaphthalene, N-cyclohexyl-2-aminonaphthalene-6-sulfonate, N-phenyl-2-aminonaphthalene-6-sulfonate, N-phenyl-N-methyl-2-aminonaphthalene-6-sulfonate, N-(o-toluyl)-2-aminonaphthalene-6-sulfonate, N-(m-toluyl)-2-aminonaphthalene-6-sulfonate, N-(p-toluyl)-2-aminonaphthalene-6-sulfonate, 2-(p-toluidinyl)-naphthalene-6-sulfonic acid (2,6-TNS), 4-(dicyanovinyl) julolidine (DCVJ), 6-dodecanoyl-2-dimethylaminonaphthalene (LAURDAN), 6-hexadecanoyl-2-(((2-(trimethylammonium)ethyl)methyl)amino) naphthalenechl oride(PATMAN), nile red, N-phenyl-1-naphthylamine, 1,1-dicyano-2-[6-(dimethylamino) naphthalen-2-yl]propene (DDNP), 4,4'-dianilino-1,1-binaphthyl-5,5-disulfonic acid (bis-ANS), and DAPOXYL.TM. derivatives (Molecular Probes, Eugene, Oreg.). Preferably for proteins, the term refers to 1,8-ANS or 2,6-TNS. Another type of fluorophore is a semiconductor nanocrystal, several nanometers in diameter, whose fluorescent properties are affected by quantum confinement effects. Such crystals are described in e.g. U.S. Pat. No. 5,990,479.

"Hybridization optimizing agent" refers to a composition that decreases hybridization between mismatched nucleic acid molecules, i.e., nucleic acid molecules whose sequences are not exactly complementary.

"Incubating " refers broadly to placing the target molecule and/or hybridization mixture in contact with the array. Preferably, incubating refers to the equilibration of binding between the target molecule and the substrate-bound molecule to be tested for binding.

"Isostabilizing agent" refers to a composition that reduces the base-pair composition dependence of DNA thermal melting transitions. More particularly, the term refers to compounds that, in proper concentration, result in a differential melting temperature of no more than about 1 C for double stranded DNA, oligonucleotides composed of AT or GC, respectively. Isostabilizing agents preferably are used at a concentration between 1 M and 10 M, between 2 M and 6 M, between 4 M and 6 M, between 4 M and 10 M and, optimally, at about 5 M. Betaines and lower tetraalkyl ammonium salts are examples of isostabilizing agents. See, U.S. Pat. No. 6,045,996, which is incorporated herein by reference.

"Oligonucleotide array" refers to a substrate having a surface having at least two different features. Oligonucleotide arrays preferably have a density of at least five hundred, at least one thousand, at least 10 thousand, at least 100 thousand, at least one million or at least 10 million features per square cm. In one embodiment, the arrays have a density of about 625 features per square cm. The substrate can be, merely by way of example, silicon or glass and can have the thickness of a glass microscope slide or a glass cover slip. Substrates that are transparent to light are useful when the method of performing an assay on the chip involves optical detection. As used herein, the term also refers to a probe array and the substrate to which it is attached that form part of a wafer.

"Probe" refers to a surface-immobilized molecule, e.g., an oligonucleotide, peptide, or protein, that can be recognized by a particular target. Depending on context, the term "probe" refers both to individual molecules and to the collection of same-sequence molecules surface-immobilized at a discrete location.

"Renaturation accelerant" refers to compounds that increase the speed of renaturation of nucleic acids by at least 100-fold. They generally have relatively unstructured polymeric domains that weakly associate with nucleic acid molecules. Accelerants include heterogenous nuclear ribonucleoprotein ("hnRP") Al and cationic detergents such as, preferably, CTAB ("cetyltrimethylammonium bromide") and DTAB ("dodecyl trimethylammonium bromide"), and, also, polylysine, spermine, spermidine, single stranded binding protein ("SSB"), phage T4 gene 32 protein and a mixture of ammonium acetate and ethanol. Renaturation accelerants can be included in hybridization mixtures at concentrations of about 1 $\mu$.M to about 10 mM and, preferably, 1 $\mu$.M to about 1 mM. The CTAB buffers work well at concentrations as low as 0.1 mM.

"Screening" refers to the testing of a multiplicity of molecules or compounds for their ability to bind to a target molecule which is capable of denaturing.

"Target" refers to a nucleic acid molecule or protein that has an affinity for a given probe. Targets may be naturally-occurring or man-made nucleic acid molecules or proteins. Also, they can be employed in their unaltered state or as aggregates with other species. Targets may be attached, covalently or noncovalently, to a binding member, either directly or via a specific binding substance. Targets are sometimes referred to in the art as anti-probes. A "Probe-Target Pair" is formed when two macromolecules have combined through molecular recognition to form a complex.

Hybridization Assays

Hybridization assays on substrate-bound oligonucleotide arrays typically involve a hybridization step and a detection step. In the hybridization step, a hybridization mixture containing the target and optionally, an isostabilizing agent, denaturing agent or renaturation accelerant is brought into contact with the probes of the array and incubated for a time appropriate to allow hybridization between the target and any complementary probes. Usually, unbound target molecules are then removed from the array by washing with a wash mixture that does not contain the target, such as hybridization buffer. This leaves only bound target molecules. In the detection step, the probes to which the target has hybridized are identified. Since the nucleotide sequence of the probes at each feature is known, identifying the locations at which target has bound provides information about the particular sequences of these probes.

The hybridization mixture includes the target nucleic acid molecule and, optionally, a hybridization optimizing agent in an appropriate solution, i.e., a hybridization buffer. The target nucleic acid molecule is present in the mixture at a concentration between about 0.005 nM target per ml hybridization mixture and about 50 nM target per ml hybridization mixture, preferably between about 0.5 nM/ml and 5 nM/ml or, more preferably, about 1 nM/ml and 2 nM/ml. The target nucleic acid molecule preferably includes a detectable label, such as a fluorescent probe molecule. Additional examples of hybridization conditions are provided in several sources, including: Sambrook et al., Molecular Cloning: A Laboratory Manual (1989), 2nd Ed., Cold Spring Harbor, N.Y.; and Berger and Kimmel, "Guide to Molecular Cloning Techniques," Methods in Enzymology, (1987), Volume 152, Academic Press, Inc., San Diego, Calif.; Young and Davis (1983) Proc. Natl. Acad. Sci. (U.S.A.) 80: 1194.

The hybridization mixture is placed in contact with the array and incubated. Contact can take place in any suitable container, for example, a dish or a flow cell specially designed to hold the array and to allow introduction of the fluid into and removal of it from the cell so as to contact the array. In a preferred embodiment, the container has a volume from approximately 50 to approximately 500 microliters. In order to achieve large temperature gradients, to increase the thermophoretic drift velocity, without recourse to excessive temperature differences, the gap between the probe surface and the opposed surface is preferably kept to a minimum. In a preferred embodiment, this gap is kept to 1 mm or less. The small gap also reduces the time needed for the analyte to drift to the reactive substrate.

The present invention generally incorporates temperature monitoring and control systems for optimization of hybridization conditions. Temperature control may be carried out by a variety of means. For example, a temperature control block may be placed adjacent to at least one of the external surfaces of the container. Preferably, the temperature gradient may be built up in such fashion that, using a controllable temperature control block, a specified temperature level is adjusted at one side of the container, while a second, spatially separated temperature level is defined by the temperature level at the opposite side. Thus, the container is connected to at least one, and preferably to two, temperature control blocks in a heat-conducting fashion.

According to one embodiment the substrate is horizontal (FIG. 1) and a vertical temperature gradient is created with the appropriate direction whereby the thermophoretic force will thus drive the DNA samples toward the lower probe surface. Circulation or agitation of the fluid may be needed for lateral redistribution.

When the lower surface is warmer than the upper surface, one might expect formation of Rayleigh-Benard convection cells, wherein buoyancy forces drive warm liquid from the bottom of the cell up to the cooler surface, where it cools, becomes more dense, and sinks back This may affect either the hybridization rate or the achievable stringency. However the onset of the Rayleigh-Benard instability is retarded when the separation between the upper and lower surfaces is small, and when the temperature difference is small. Therefore Rayleigh-Benard convection may be absent in some embodiments of this invention.

Figure 2:
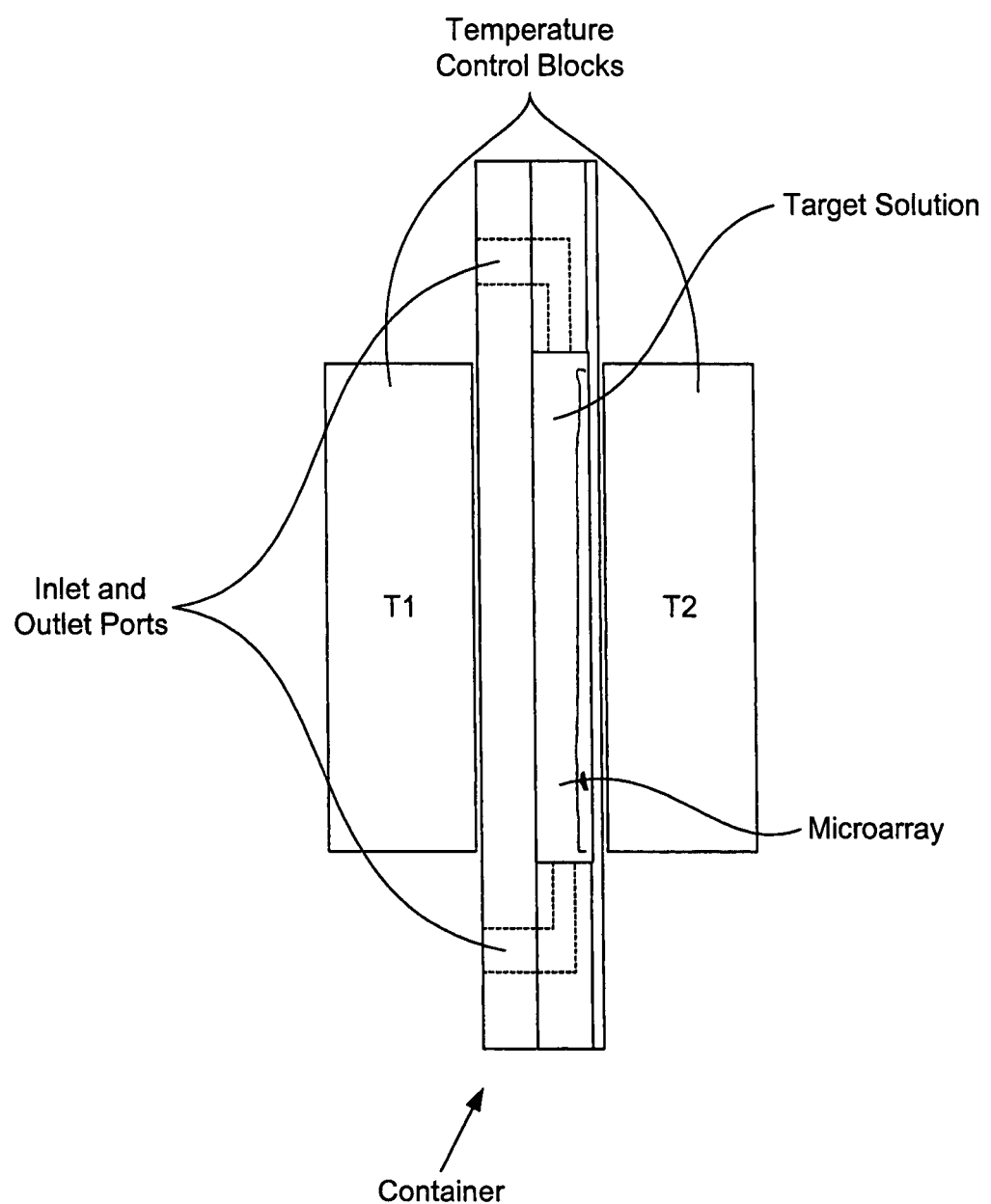
FIG. 2 shows an embodiment of the invention wherein a hybridization cell oriented vertically is installed between two temperature reservoirs.
Figure 3:
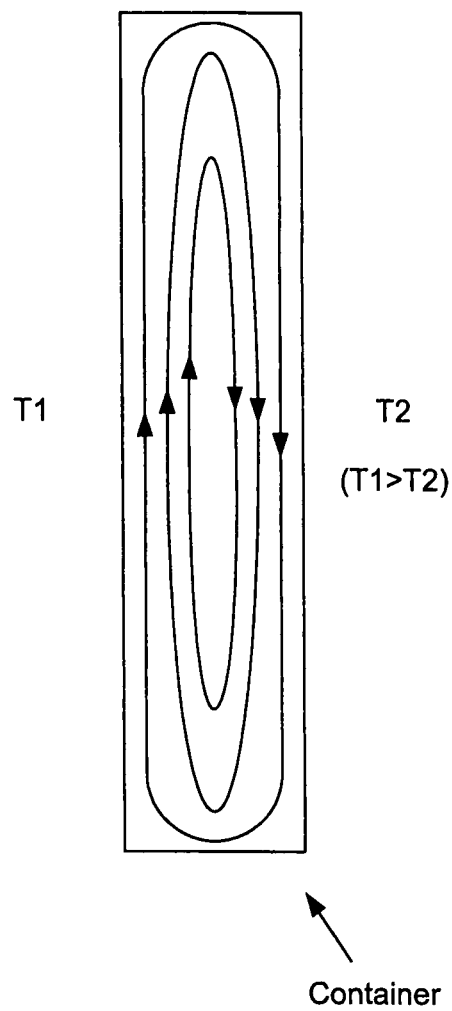
FIG. 3 illustrates a free convection circulation flow that may occur when the hybridization cell is oriented as shown in FIG. 2.

In another embodiment, the cell is oriented vertically (FIG. 2) and some free convection will take place. The circulation will probably be similar to that shown in FIG. 3. This flow, which includes the DNA molecules, is superimposed on the horizontal thermophoretic drift of the DNA toward or away from the oligonucleotide substrate. The free convection flow may assist lateral redistribution of the DNA molecules.

The desired temperature gradient is maintained within the container by thermal exchange across the relatively thin walls of the container against which one or more temperature controller blocks are placed. The thickness of the wall is typically dependent upon a number of factors including, e.g., the composition of the material, the desired temperature range, the thermal conductivity of the wall, manufacturing tolerances, and the like.

Generally, incubation will be at temperatures normally used for hybridization of nucleic acids, for example, between about 20° C. and about 75° C., e.g., about 25° C., about 30° C., about 35° C., about 40° C., about 45° C., about 50° C., about 55° C., about 60° C. or about 65° C. For probes longer than about 14 nucleotides, 37° C. -45° C. is preferred. For shorter probes, 55° C.-65° C. is preferred.

Preferably, a temperature gradient of between about 5 and 25° C./mm, more preferably, between about 5 and 15° C./mm, and most preferably, a temperature gradient of about 10° C./mm will be used.

The target is incubated with the probe array for a time sufficient to allow the desired level of hybridization between the target and any complementary probes in the array. Using a hybridization temperature of 25° C. and with a 10° C./mm temperature gradient yields a very clear signal, usually in at least 30 minutes to two hours, but it may be desirable to hybridize longer, i.e., about 15 hours.

In preferred aspects, the temperature control block may be a thermoelectric temperature controller, e.g., a Peltier heater/cooler. Alternatively, a temperature control block may incorporate a series of channels through which is flowed a recirculating temperature controlled fluid, e.g., water, ethylene glycol or oil, which is heated or cooled to a desired temperature, e.g., in an attached water bath. The temperature control blocks may be time-controllable.

Exemplary heating elements include resistive heaters, such as an 80 W HD04-0100N heater available from Heater Cartridge, Wooddale, Ill. Exemplary cooling elements includes Peltier crystals (which can cool the plate to about −20degrees C.), frozen substances, and the like. One exemplary Peltier device is model TE 9501/127/030B, available from Melcor Thermoelectrics. One or more water baths capable of being thermostatted can also be used as a heating or cooling element. Such elements may be placed directly against the container or within a thermally conductive material which is in direct contact with the container.

The system may also include a temperature control element to preheat or precool fluids prior to injection into the container. For example, the reagent/sample vessels may be placed in a temperature controlled environment, e.g., a water bath, to achieve optimal pre-injection temperatures. Alternatively, an in-line temperature controller may be employed to adjust the temperature of the fluid as it is being delivered to the container. Typically, this involves the use of a coiled heat-exchange tube as part of the fluid passage. The heat-exchange coil is generally disposed around a temperature controlled element and is fabricated from a material having a relatively high thermal transfer coefficient, e.g., stainless steel, copper, aluminum, etc.

The container preferably includes an aperture which permits optical access to the array. The aperture or window may be a quartz, or other suitable material chose in part for its transmission and non-fluorescence properties. Advantageously, the window is chosen to have an index of refraction which substantially matches the index of refraction of the sample solution.

An inlet port and an outlet port may be provided through the flow cell. An input tube is preferably connected to the inlet port. Optionally, the input tube connects to a fluidic interface port, such as formed by a female Luer taper system. An output tube is preferably connected to the outlet port. The components of the fluidic system are preferably formed from inert materials, e.g., tetrafluoroethylene, or other medical grade plastics. The flow cell and associated components may be formed through any known technique, such as molding or machining. The output tube preferably provides a communication path from the flow cell to a reservoir.

After the desired reaction is complete, the array usually is washed with the hybridization buffer, which also can include the hybridization optimizing agent. These agents can be included in the same range of amounts as for the hybridization step, or they can be eliminated altogether. Preferably, the temperature gradient is also reversed thereby creating a thermophoretic force in the direction opposite to the prior attractive force. In this way, nonspecific analytes or unreacted molecules may be removed from the array. Specific analytes or reaction products may be released from any array or feature thereof and transported to other locations for further analysis; or stored at other addressable locations; or removed completely from the system. This removal or deconcentration of materials by reversal of the force enhances the discrimination ability of the system by resulting in removal of nonspecifically bound materials. By controlling the amount of now repulsive thermophoretic force to nonspecifically bound materials on the array, stringency control may be achieved. By increasing the temperature gradient so as to remove partially hybridized DNA sequences, thereby permitting identification of single mismatched hybridizations, point mutations may be identified.

Preparation of Target Samples

The target polynucleotide whose sequence is to be determined is usually isolated from a tissue sample. If the target is genomic, the sample may be from any tissue (except exclusively red blood cells). For example, whole blood, peripheral blood lymphocytes or PBMC, skin, hair or semen are convenient sources of clinical samples. These sources are also suitable if the target is RNA. Blood and other body fluids are also a convenient source for isolating viral nucleic acids. If the target is mRNA, the sample is obtained from a tissue in which the mRNA is expressed. If the polynucleotide in the sample is RNA, it is usually reverse transcribed to DNA. DNA samples or cDNA resulting from reverse transcription are usually amplified, e.g., by PCR. Depending on the selection of primers and amplifying enzyme(s), the amplification product can be RNA or DNA. Paired primers are selected to flank the borders of a target polynucleotide of interest. More than one target can be simultaneously amplified by multiplex PCR in which multiple paired primers are employed.

The target can be labeled at one or more nucleotides during or after amplification. For some target polynucleotides (depending on size of sample), e.g., episomal DNA, sufficient DNA is present in the tissue sample to dispense with the amplification step. Preferably, the detectable label is a luminescent label. Useful luminescent labels include fluorescent labels (or fluorescent probe molecules), chemi-luminescent labels, bio-luminescent labels, and colorimetric labels, among others. Most preferably, the label is a fluorescent probe molecule such as a fluorescein, a rhodamine, a polymethine dye derivative, a phosphor, and so forth. Commercially available fluorescent labels include, inter alia, fluorescein phosphoramidites such as Fluoreprime (Pharmacia, Piscataway, N.J.), Fluoredite (Millipore, Bedford, Mass.) and FAM (ABI, Foster City, Calif.).

Many alternatives to the detection of hybridized DNA by fluorescence exist. Most of the alternative techniques also involve modification of capture or target or reporter DNA probes with reporter groups that produce a detectable signal. A few of these techniques based on purely physical measurements do not require reporter groups. These alternative techniques are catalogued as follows: (1) Linear Optical Methods including fluorescence, time modulated fluorescence, fluorescence quenching modulation, polarization selective fluorescence, absorption, specular reflectance, changes in index of refraction, ellipsometry, surface plasmon resonance detection, chemiluminescence, speckle interferometry and magneto-optic Kerr effect; (2) Nonlinear Optical Methods including second harmonic generation, third harmonic generation, parametric mixing, optical heterodyne detection, phase conjugation, soliton damping and optical Kerr effect; (3) Methods Based on Thermal Effects including differential scanning calorimetry, multifrequency differential scanning calorimetry, and differential thermal analysis; (4) Methods Based on Mass Changes including crystal microbalances, cantilever microbalances, surface acoustic waves and surface Love waves; (5) Electrochemical Methods including amperometry, coulometry, voltammetry, electrochemiluminescence, charge transfer in donor-acceptor complexes and surface impedance spectroscopy; and (6) Radioactivity Detection Methods using labeled group.

More specifically, useful light scattering labels include large colloids, and especially the metal colloids such as those from gold, selenium and titanium oxide. Radioactive labels include, for example, $^{32}P$. This label can be detected by a phosphoimager. Detection, of course, depends on the resolution of the imager. Phosphoimagers are available having resolution of 50 microns. Accordingly, this label is currently useful with chips having features of at least that size.

When the target strand is prepared in single-stranded form as in preparation of target RNA, the sense of the strand should of course be complementary to that of the probes on the chip. This is achieved by appropriate selection of primers. The target is preferably fragmented before application to the chip to reduce or eliminate the formation of secondary structures in the target. The average size of target segments following hybridization is usually larger than the size of the probe on the chip.

Substrate-Bound Oligonucleotide Arrays

Substrate-bound oligonucleotide arrays used in the assays of this invention typically include between about $5 \times 10^2$ and about $10^8$ features per square centimeter, or between about $10^4$ and about $10^7$ or between about $10^5$ and $10^6$.

The construction of solid phase biopolymer arrays is well described in the literature. See, e.g., Merrifield (1963) J. Am. Chem. Soc. 85: 2149-2154 (describing solid phase synthesis of, e.g., peptides); Geysen. et al. (1987) J. Immun. Meth. 102: 259-274 (describing synthesis of solid phase components on pins). See, Frank and Doring (1988) Tetrahedron 44: 6031-6040 (describing synthesis of various peptide sequences on cellulose disks); Fodor et al. (1991) Science 251: 767-777; Southern et al. (1992) Genomics 13: 1008-1017; Sheldon et al. (1993) Clinical Chemistry 39(4): 718-719 and Kozal et al. (1996) Nature Medicine 2(7): 753-759 (all describing arrays of biopolymers fixed to solid substrates).

Preferably, the arrays are produced through spatially directed oligonucleotide synthesis. Methods for production of such arrays are well known in the art and include any method of directing the synthesis of an oligonucleotide to a specific location on a substrate. Methods for spatially directed oligonucleotide synthesis include, without limitation, light-directed oligonucleotide synthesis, microlithography, application by ink jet, microchannel deposition to specific locations and sequestration with physical barriers.

In making a chip, the substrate and its surface preferably form a rigid support on which the sample can be formed. The substrate and its surface are also chosen to provide appropriate light-absorbing characteristics. For instance, the substrate may be functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, or combinations thereof. Other substrate materials will be readily apparent to those skilled in the art upon review of this disclosure. In a preferred embodiment the substrate is flat glass or silica. Surfaces on the solid substrate usually, though not always, are composed of the same material as the substrate. Thus, the surface may be composed of any of a wide variety of materials, for example, polymers, plastics, resins, polysaccharides, silica or silica-based materials, carbon, metals, inorganic glasses, membranes, or any of the above-listed substrate materials. In one embodiment, the surface will be optically transparent and will have surface Si-OH functionalities, such as those found on silica surfaces. Preferably, oligonucleotides are arrayed on a chip in addressable rows and columns. Technologies already have been developed to read information from such arrays. The amount of information that can be stored on each chip depends on the lithographic density which is used to synthesize the wafer. For example, if each feature size is about 00 microns on a side, each chip can have about 10,000 probe addresses (features) in a 1 cm² area.

Binding Assays

The methods described herein can also be used to facilitate ELISAs or other binding assays wherein one binding partner is immobilized on a solid support and the other is present in solution. As described above, methods for preparing arrays of biomolecules, including peptides, proteins, antibodies, and oligonucleotides are well known in the art.

The assay mixture can also include a variety of other reagents, such as salts, buffers, neutral proteins, e.g., albumin, detergents, and the like, which may be used to facilitate optimal protein-protein binding and/or reduce non-specific or background interactions, etc. Reagents that otherwise improve the efficiency of the assay, such as protease inhibitors, nuclease inhibitors, antimicrobial agents, and the like, can also be used. The mixture components can be added in any order that provides for the requisite bindings.

Generally, incubation will be at temperatures used for such binding assay acids, for example, between about 20° C. and about 75° C., e.g., about 25° C., about 30° C., about 35° C., about 40° C., about 45° C., about 50° C., about 55° C., about 60° C. or about 65° C. Preferably, a temperature of 37° C.-45° C. will be used.

Preferably, a temperature gradient of between about 5 and 25° C./mm, more preferably, between about 5 and 15° C./mm, and most preferably, a temperature gradient of about 10° C./mm will be used.

Incubation periods are likewise selected for optimal binding but also minimized to facilitate rapid, high-throughput screening, and are typically between 1 and 10 hours, preferably less than 5 hours, more preferably less than 2 hours. For optimal high throughput applications, the reaction is carried out for between 0.1 and 4 hours, more typically between about 0.5 and 1.5 hours.

After incubation, it may be desirable to separate any unbound target from the array. Typically, the separation step will include an extended rinse or wash or a plurality of rinses or washes. For example, the array may be washed several times with a washing solution, which typically includes those components of the incubation mixture that do not participate in specific binding such as salts, buffer, detergent, nonspecific protein, etc. In addition the temperature gradient may be reversed, so that thermophoretic forces assist in separating the unbound target from the array.

Detection can be effected in any convenient way. Frequently, one of the components, generally, the target, comprises or is coupled to a label. The assay component can be either directly labeled, i.e., comprise or react to produce a detectable label, or indirectly labeled, i.e., bind to a molecule comprising or reacting to produce a detectable label. Labels can be directly attached to or incorporated into the assay component or detection moiety by chemical or recombinant methods.

More specifically, the detectable labels used in the assays of the present invention, can be primary labels (where the label comprises an element that is detected directly or that produces a directly detectable element) or secondary labels (where the detected label binds to a primary label, e.g., as is common in immunological labeling). An introduction to labels, labeling procedures and detection of labels is found in Polak and Van Noorden (1997) Introduction to Immunocytochemistry, 2nd ed., Springer Verlag, N.Y. and in Haugland (1996) Handbook of Fluorescent Probes and Research Chemicals, a combined handbook and catalogue Published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green.TM., rhodamine and derivatives (e.g., Texas red, tetrarhodimine isothiocynate (TRITC), etc.), digoxigenin, biotin, phycoerythrin, AMCA, CyDyes.TM., and the like), radiolabels (e.g., $^{3}$H, 125I, $^{35}$S, $^{14}$C, $^{32}$P, $^{33}$P, etc.), enzymes (e.g., horseradish peroxidase, alkaline phosphatase etc.), spectral colorimetric labels such as colloidal gold or colored glass or plastic (e.g. polystyrene, polypropylene, latex, etc.) beads. The label may be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Preferred labels include those that use: 1) chemiluminescence (using horseradish peroxidase or luciferase) with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate (kits available from Life Technologies/Gibco BRL, and Boehringer-Mannheim)); 3) chemifluorescence using, e.g., alkaline phosphatase and the substrate AttoPhos (Amersham) or other substrates that produce fluorescent products, 4) fluorescence (e.g., using Cy-5 (Amersham), fluorescein, and other fluorescent tags); 5) radioactivity. Other methods for labeling and detection will be readily apparent to one skilled in the art.

Preferred enzymes that can be conjugated to detection reagents of the invention include, e.g., .beta.-galactosidase, luciferase, and horseradish peroxidase. The chemiluminescent substrate for luciferase is luciferin. One embodiment of a chemiluminescent substrate for .beta.-galactosidase is 4-methylumbelliferyl-.beta.-D-galactoside. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3,2'-adamantane], which is detected with a luminometer. Embodiments of horseradish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

In general, a detector which monitors a particular label is used to detect the label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

Most typically, binding of the target molecule to the corresponding immobilized binding partner is measured by quantitating the amount of label fixed to the solid support by binding of the detection reagent. Typically, presence of a modulator during incubation will increase or decrease the amount of label fixed to the solid support relative to a control incubation which does not comprise the modulator, or as compared to a baseline established for a particular assay type. Means of detecting and quantitating labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes and many other detection systems which are widely available.

The references discussed herein are provided solely for their disclosure prior to the filing date of the present application and are each incorporated herein by reference. Nothing herein is to be construed as an admission that the inventors are not entitled to antedate such disclosure by virtue of prior invention.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes are carrying out the invention which are obvious to those skilled in the art are intended to be within the scope of the following claims.

What is claimed is:

1. A method for performing a hybridization assay between target biomolecules and an array, the array comprising a surface to which are attached biomolecular probes with different, known sequences, at discrete, known locations, the method comprising:
providing a container holding a hybridization mixture comprising the target biomolecules and also holding the array; and
creating a temperature gradient in the hybridization mixture such that a thermophoretic force acts upon the target biomolecules to move the target biomolecules from the warmer portion of the mixture to the cooler portion of the mixture, wherein the temperature gradient is oriented within the container such that the target biomolecules are driven by the thermophoretic force onto the surface of the array.

2. The method of claim 1, wherein the target biomolecules further comprise a detectable label.

3. The method of claim 2, wherein the label is a fluorescent probe molecule.

4. The method of claim 3, wherein the fluorescent probe molecule is fluorescein.

5. The method of claim 1, wherein the array has a density of at least ten thousand features per square cm.

6. The method of claim 5, wherein the array has a density of at least one hundred thousand features per square cm.

7. The method of claim 6, wherein the array has a density of at least one million features per square cm.

8. The method of claim 1, wherein the temperature gradient is oriented perpendicular to the array surface.

9. The method of claim 8, wherein the array surface is vertical and the temperature gradient is horizontal.

10. The method of claim 8, wherein the array surface is horizontal and the temperature gradient is vertical.

11. The method of claim 1, wherein the temperature gradient is between about 5 and 25° C./mm.

12. The method of claim 1, wherein the hybridization mixture further comprises an isostabilizing agent.

13. The method of claim 1, wherein the temperature gradient is between about 5 and 15° C./mm.

14. The method of claim 1, wherein the temperature gradient is about 10° C./mm.

15. The method of claim 1, further comprising incubating the hybridization mixture with the array for a period of time at a hybridization temperature sufficient to allow hybridization of the target biomolecules to the biomolecular probes on the surface of the array.

16. The method of claim 15, wherein the incubation period is from thirty minutes to two hours.

17. The method of claim 15, wherein the hybridization temperature is about 25° C.

18. The method of claim 15, wherein the hybridization temperature is from about 20° C. to about 75° C.

19. The method of claim 15, wherein the hybridization temperature is in the range of 37° C. to 45° C.

20. The method of claim 15, wherein the hybridization temperature is from about 55° C. to about 65° C.

21. The method of claim 1, further comprising reversing the temperature gradient, wherein the reversed temperature gradient is oriented within the container such that a reversed thermophoretic force acts upon unhybridized target biomolecules to move the unhybridized target biomolecules from the warmer portion of the mixture to the cooler portion of the mixture, wherein the reversed temperature gradient is oriented within the container such that the unhybridized target biomolecules are driven by the reversed thermophoretic force away from the surface of the array.

22. The method of claim 1, further comprising determining the sequences of biomolecular probes to which the target biomolecules have hybridized.

23. The method of claim 1, wherein the target biomolecules are selected from peptides, proteins, nucleic acids, antibodies, and oligonucleotides.

24. The method of claim 1, wherein the method further comprises reversing the temperature gradient, wherein the reversed temperature gradient is oriented within the container such that a reversed thermophoretic force acts upon unhybridized target biomolecules to move the unhybridized target biomolecules from the warmer portion of the mixture to the cooler portion of the mixture, wherein the reversed temperature gradient is oriented within the container such that the unhybridized target biomolecules are driven by the reversed thermophoretic force away from the surface of the array; and
the method further comprises determining the sequences of biomolecular probes to which the target biomolecules have hybridized;
wherein the target biomolecules further comprise a detectable fluorescein label, the array has a density of at least ten thousand features per square cm, the array surface is vertical and the temperature gradient is horizontal, the hybridization mixture further comprises lower tetraalkyl ammonium salts, and the target biomolecule is a nucleic acid.

25. The method of claim 15, wherein the method further comprises reversing the temperature gradient, wherein the reversed temperature gradient is oriented within the container such that a reversed thermophoretic force acts upon unhybridized target biomolecules to move the unhybridized target biomolecules from the warmer portion of the mixture to the cooler portion of the mixture, wherein the reversed temperature gradient is oriented within the container such that the unhybridized target biomolecules are driven by the reversed thermophoretic force away from the surface of the array; and
    the method further comprises determining the sequences of biomolecular probes to which the target biomolecules have hybridized;
  wherein the target biomolecules further comprise a detectable fluorescein label, the array has a density of at least ten thousand features per square cm, the array surface is vertical and the temperature gradient is horizontal, the hybridization mixture further comprises lower tetraalkyl ammonium salts, and the target biomolecule is a nucleic acid.

26. The method of claim 1, wherein the gap between the surface of the array and the opposed surface of the container is 1 mm or less.

\* \* \* \* \*